(12) United States Patent
Kono et al.

(10) Patent No.: US 11,064,935 B2
(45) Date of Patent: Jul. 20, 2021

(54) PHOTOSENSITIVITY TEST DEVICE

(71) Applicants: NATIONAL UNIVERSITY CORPORATION NAGOYA UNIVERSITY, Aichi-ken (JP); NIKKISO CO., LTD., Tokyo (JP)

(72) Inventors: Michihiro Kono, Nagoya (JP); Masashi Akiyama, Nagoya (JP); Yasushi Ogawa, Nagoya (JP); Hideki Asano, Hakusan (JP); Suguru Mishina, Toyko (JP); Satoru Matsuzawa, Toyko (JP)

(73) Assignees: NATIONAL UNIVERSITY CORPORATION NAGOYA UNIVERSITY, Nagoya (JP); NIKKISO CO., LTD, Tokyo (JP)

( * ) Notice: Subject to any disclaimer, the term of this patent is extended or adjusted under 35 U.S.C. 154(b) by 507 days.

(21) Appl. No.: 15/920,058

(22) Filed: Mar. 13, 2018

(65) Prior Publication Data
US 2018/0206779 A1    Jul. 26, 2018

Related U.S. Application Data

(63) Continuation of application No. PCT/JP2016/075011, filed on Aug. 26, 2016.

(30) Foreign Application Priority Data

Sep. 17, 2015    (JP) .............................. JP2015-184239

(51) Int. Cl.
*A61B 5/00* (2006.01)
*A61N 5/06* (2006.01)

(52) U.S. Cl.
CPC ............ *A61B 5/441* (2013.01); *A61B 5/0064* (2013.01); *A61B 2560/0214* (2013.01);
(Continued)

(58) Field of Classification Search
None
See application file for complete search history.

(56) References Cited

U.S. PATENT DOCUMENTS 6,443,945 B1 * 9/2002 Marchitto .............. A61B 5/411
606/7
6,989,023 B2 * 1/2006 Black ................. A61H 23/0245
607/88
(Continued)

FOREIGN PATENT DOCUMENTS

CN    2719223 Y    8/2005
CN    1768876 A    5/2006
(Continued)

OTHER PUBLICATIONS

Mountford et al.; "An On-Line Ultraviolet Radiation Monitoring System for Control of Photosensitivity Test Dose"; Phys. Med. Biol.; 1984; vol. 29; No. 4; pp. 407-417; Great Britian.
(Continued)

*Primary Examiner* — Bill Thomson
*Assistant Examiner* — Younhee Choi
(74) *Attorney, Agent, or Firm* — Muncy, Geissler, Olds & Lowe, PC

(57) ABSTRACT

A test device is used to test photosensitivity of a skin. The test device is provided with an irradiation unit including a plurality of light irradiation units arranged in a first direction. The plurality of light irradiation units output, in a second direction intersecting the first direction, irradiation light beams that mutually differ at least in one of wavelength characteristics and intensity. The irradiation unit is configured such that intensities of the irradiation light beams output from the plurality of light irradiation units are progressively smaller in the first direction.

4 Claims, 13 Drawing Sheets

(52) U.S. Cl.
CPC ..... *A61B 2562/0242* (2013.01); *A61N 5/0616* (2013.01); *A61N 2005/0628* (2013.01)

(56) References Cited

U.S. PATENT DOCUMENTS

| | | | |
|---|---|---|---|
| 7,963,985 B2 * | 6/2011 | Minamoto | A61B 5/445 607/94 |
| 2002/0128696 A1 | 9/2002 | Pearl et al. | |
| 2003/0093915 A1 * | 5/2003 | Pearl | A61N 5/0617 34/96 |
| 2008/0183162 A1 | 7/2008 | Altshuler et al. | |
| 2010/0079587 A1 * | 4/2010 | Yoshida | A61B 1/0638 348/68 |
| 2015/0099980 A1 * | 4/2015 | Nahman | A61B 5/0507 600/475 |
| 2015/0111287 A1 | 4/2015 | Rawle | |

FOREIGN PATENT DOCUMENTS

| | | |
|---|---|---|
| CN | 101097261 A | 1/2008 |
| CN | 101828102 A | 9/2010 |
| CN | 102176864 A | 9/2011 |
| EP | 1637077 A1 | 3/2006 |
| EP | 1637077 A1 | 3/2006 |
| JP | 50-4987 B1 | 2/1975 |
| JP | 50-4988 B1 | 2/1975 |
| JP | H0788113 A | 4/1995 |
| JP | 2006000383 A | 1/2006 |
| JP | 2006087472 A | 4/2006 |
| JP | 2010005438 A | 1/2010 |
| WO | WO-2006/049192 A1 | 5/2006 |
| WO | WO-2006049192 A1 * | 5/2006 ............. A61B 5/441 |
| WO | WO-2013/133725 A1 | 9/2013 |
| WO | WO2013/186780 A1 | 12/2013 |

OTHER PUBLICATIONS

Supplementary European Search Report Based on Application No. EP 16846228; dated Feb. 12, 2019.
Japanese Patent Office, Office Action, dated Jan. 15, 2019, 3 pages, with English translation (5 pages).
Mountford et al., "An on-line ultraviolet radiation monitoring system for control of photosensitivity test dose," Phys. Med. Biol., 1984, vol. 29, No. 4, pp. 407-417, 11 pages.
Chinese Office Action based on corresponding Application No. 201680052537.X; dated Mar. 16, 2020.
Office Action and Search Report of the corresponding to Chinese application No. CN201680052537.X dated Dec. 3, 2020. (pp. 15 ).

* cited by examiner

FIG. 10
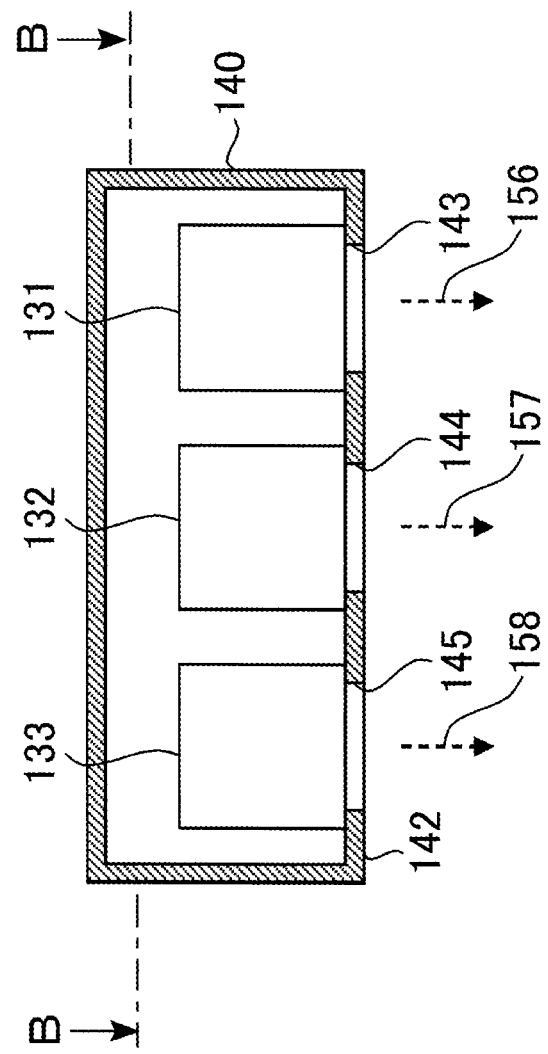
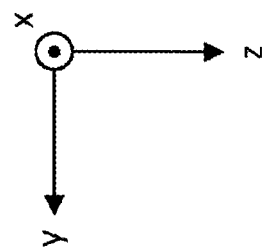

PHOTOSENSITIVITY TEST DEVICE

RELATED APPLICATION

This application is a Continuation of co-pending International Application No. PCT/JP2016/075011 filed Aug. 26, 2016, for which priority is claimed under 35 U.S.C. § 120; and this application claims priority of Application No. 2015-184239 filed in Japan on Sep. 17, 2015 under 35 U.S.C. § 119; the entire contents of all of which are hereby incorporated by reference.

BACKGROUND

1. Field of the Invention

The present invention relates to test devices for medical uses and, more particularly, a test device for configuring an initial condition for diagnosis of photosensitivity and for light treatment.

2. Description of the Related Art

There is a close relationship between dermatology and ultraviolet light. Ultraviolet light has long been used to treat not only a disease called photosensitivity caused by ultraviolet but also to treat refractory illnesses such as skin cancer exemplified by malignant skin lymphocyte tumor, plaque psoriasis, vitiligo vulgaris, atopic dermatitis, etc. Photosensitivity is excessive reaction of the skin to ultraviolet light or visible light. A photosensitivity test determines the wavelength at which the skin is sensitive and how sensitive the skin is. Ultraviolet is used in treatment by irradiating the affected part of the body with long-wavelength ultraviolet light (UVA wave) or middle-wavelength ultraviolet light (UVB wave) with a predetermined energy level. The amount of ultraviolet irradiation energy that induces reaction by the skin varies from person to person with or without photosensitivity. For this reason, a photosensitivity test is performed to determine a suitable irradiance level before ultraviolet treatment.

In a photosensitivity test, the minimum irradiance that induces reaction by the skin is determined by irradiating the healthy skin with ultraviolet or visible light, shifting the positon and varying the irradiance level. For example, the healthy skin of a patient is irradiated by ultraviolet light via a porous plate provided with a plurality of window holes. By closing the window holes selectively in accordance with the irradiance level or irradiation time of ultraviolet light, the irradiation level of ultraviolet light radiated via the respective window hole is regulated.

In the aforementioned test method using a porous plate, a large sized irradiation device for ultraviolet treatment is often used as a light source. In most cases, the porous plate is placed on the back of a patient lying on a bed and ultraviolet light is radiated accordingly. Often, the porous plate is not firmly fixed. Also, the subject should remain still during the irradiation time since it is necessary to maintain the distance between the light source for radiating light and the skin of the subject to be constant. As a result, it has been practically impossible to perform a test in the case of young children, elderly people, and patients with other diseases who have difficulty to maintain the same posture for a long period of time. Further, it has been occasionally impossible to obtain accurate test results due to a shift in the position of the porous plate caused by the body movement during the test or a shift in the distance from the light source. Inaccurate test results in these cases not only lead to erroneous diagnosis or treatment but may cause an increase in the light dose that may result in skin disorder or irradiation on a portion outside the target.

Photosensitivity tests have been performed from long ago for the purpose of diagnosis or treatment. In practice, however, not all patients that require testing have been tested because the devices are bulky and an accurate determination is often impossible despite considerable effort required of doctors or heavy burden on patients. Further, bulkiness of the devices has made it sometimes difficult to install a device in a small facility like an ambulatory clinic or in an ordinary clinic. Still further, only limited facilities have been able to make the entire lineup of devices available to test at a variety of wavelengths. One may use a device designed to irradiate a portion of the skin with a spot of ultraviolet light. However, ultraviolet irradiation need be repeated by changing the irradiation condition in five to eight stages. Therefore, the work volume and time required for tests are increased and the burden on doctors and patients is increased as compared to the method using a porous plate. It cannot therefore be said that the use of such a device is practical.

SUMMARY OF THE INVENTION

In this background, one illustrative purpose of the present invention is to provide a test device capable of reducing the burden on doctors and patients in photosensitivity tests and realizing more safe and accurate tests.

A test device according to an embodiment of the present invention for testing photosensitivity of a skin, comprises: an irradiation unit including a plurality of light irradiation units arranged in a first direction. The plurality of light irradiation units output, in a second direction intersecting the first direction, irradiation light beams that mutually differ at least in one of wavelength characteristics and intensity.

According to the embodiment, a plurality of irradiation light beams having different wavelength characteristics or intensities can be output at the same time. Therefore, the light used in the test can be radiated to different portions on the skin with different intensities at the same time. For example, by making five to eight light irradiation units available, sessions of ultraviolet irradiation at irradiance levels of five to eight stages required for the test can be performed at the same time. By changing the wavelength characteristics of the light irradiation units, sessions of light irradiation with different wavelengths required for the test can be performed at the same time. This can reduce the burden on doctors and patients in the test.

The irradiation unit may be configured such that intensities of the irradiation light beams output from the plurality of light irradiation units are progressively smaller in the first direction.

The test device may further comprise a frame body that extends in the second direction so as to individually surround the irradiation light beams output from the plurality of light irradiation units respectively.

The test device may further comprise a plurality of light emitting devices. Each of the plurality of light emitting devices may emit the irradiation light beam emitted from a corresponding one of the light irradiation units.

The test device may further comprise a light source unit. The irradiation unit may include a plurality of beam splitters arranged in the first direction, split a light from the light source unit into a plurality of irradiation light beams having different intensities by using the plurality of beam splitters, and cause corresponding ones of light irradiation units to output the irradiation light beams thus split.

The light source unit may include a plurality of light emitting devices having different central wavelengths or peak wavelengths, synthesize the light output from the plurality of light emitting devices, and output the synthesized light to the irradiation unit.

The light source unit may be a first light source unit that outputs a first test light including ultraviolet light of a first wavelength band, and the irradiation unit may be a first irradiation unit that splits the first test light into a plurality of first irradiation light beams and outputs the irradiation light beams thus split in the second direction intersecting the first direction. The test device may further comprise: a second light source unit that outputs a second test light including ultraviolet light of a second wavelength band more toward the long wavelength side than the first wavelength band; a third light source that outputs a third test light including visible light; a second irradiation unit that includes a plurality of beam splitters arranged in the first direction, and splits the second test light into a plurality of second irradiation light beams and outputs the irradiation light beams thus split in the second direction; and a third irradiation unit that includes a plurality of beam splitters arranged in the first direction, and splits the third test light in to a plurality of third irradiation light beams and outputs the irradiation light beams thus split in the second direction. The first irradiation unit, the second irradiation unit, and the third irradiation unit may be arranged in a third direction intersecting both the first direction and the second direction.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 10 is a sectional view schematically showing a configuration of the test device of FIG. 9;

DETAILED DESCRIPTION OF THE INVENTION

Described below is an explanation of the embodiments of the present invention with reference to figures. In the figures, like numerals represent like constituting elements, and the description thereof is omitted appropriately.

A detailed description of an embodiment to implement the present invention will be given with reference to the drawings. Like numerals are used in the description to denote like elements and the description is omitted as appropriate.

First Embodiment

Figure 1:
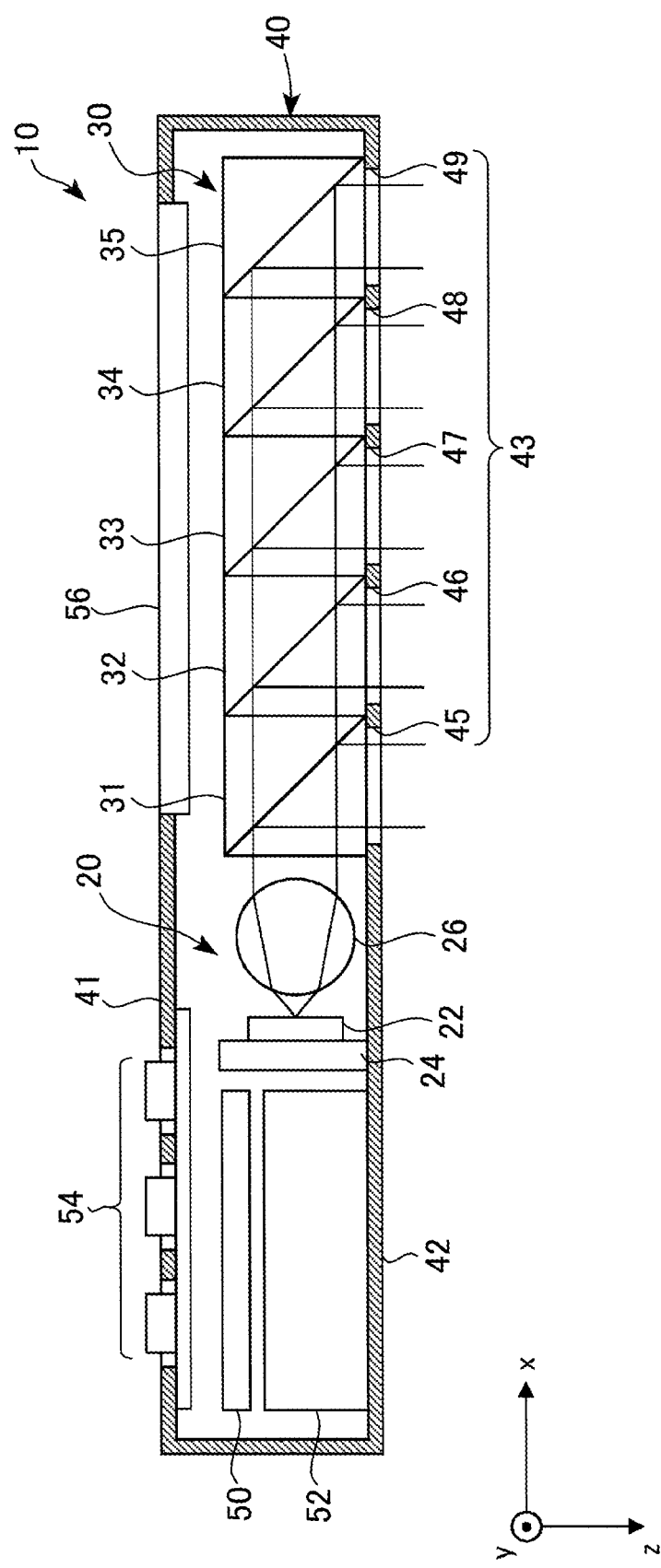
FIG. 1 schematically shows a configuration of a test device according to the first embodiment.
Figure 2:
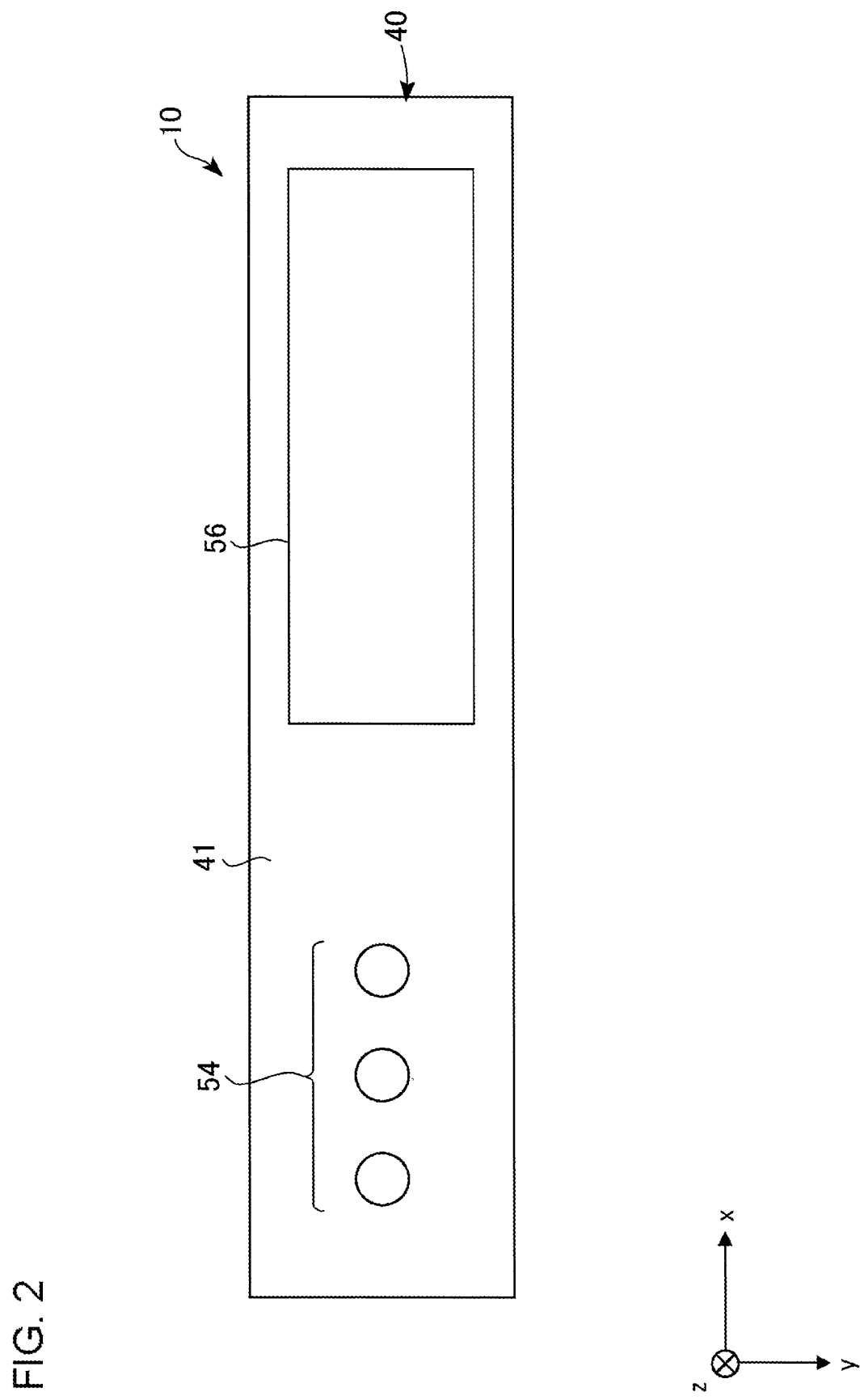
FIG. 2 is a top view schematically showing a configuration of the test device of FIG. 1.
Figure 3:
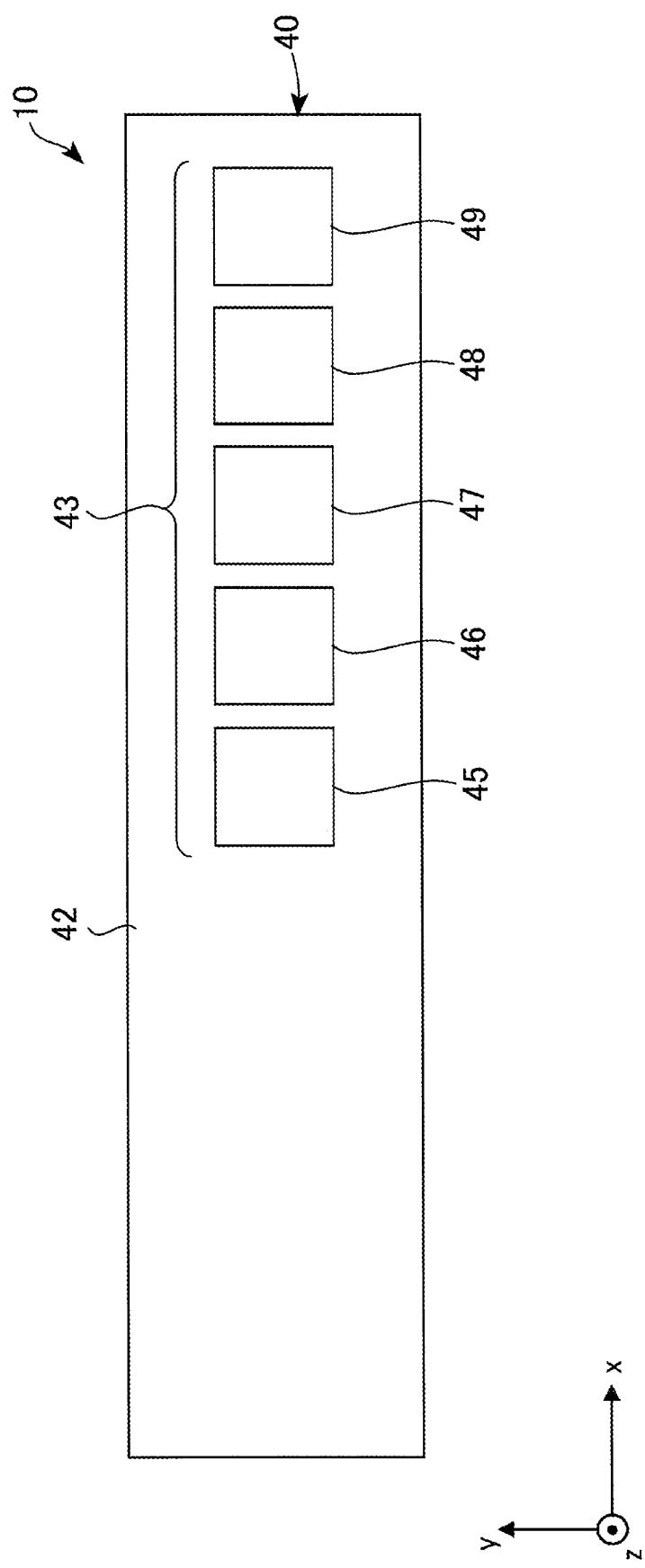
FIG. 3 is a bottom view schematically showing a configuration of the test device of FIG. 1.

FIG. 1 schematically shows a configuration of a test device 10 according to the first embodiment. FIG. 2 shows the test device 10 as viewed from above a top surface 41, and FIG. 3 shows the test device 10 as viewed from below a bottom surface 42. The test device 10 is used for a test in which the patient's skin is irradiated by a plurality of irradiation light beams output from openings 43 to determine Minimal Erythema Dose (MED), which is the minimum irradiance level that produces erythema, a Minimal Response Dose (MRD), or Minimal Phototoxic Dose (MPD). Such a test is also referred to as a photosensitivity test and is performed to determine an ultraviolet irradiance level suited to the diagnosis or ultraviolet treatment of a patient with photosensitivity before irradiation. In a test to diagnose photosensitivity, visible light as well as ultraviolet light is used.

The test device 10 includes a light source unit 20, an irradiation unit 30, a housing 40, a controller 50, a power supply 52, a user control unit 54, and a display unit 56.

The light source unit 20 includes a light emitting device 22, a substrate 24, and a collimator lens 26. For example, the light emitting device 22 is a light emitting diode (LED) configured to output a light of a wavelength used in photosensitivity tests. The light emitting device 22 outputs a 320 nm-400 nm long-wavelength ultraviolet light (UVA wave), a 290 nm-320 nm middle-wavelength ultraviolet light (UVB wave), or the like used in ultraviolet treatment. The light emitting device 22 implemented by an LED of a central central wavelength or peak wavelength of about 305 nm can be used for a test using UVB waves. Aluminum gallium nitride (AlGaN) based LEDs are known as such LEDs.

The light emitting device 22 is mounted on the substrate 24. The substrate 24 is made of a highly exoergic metal such as copper (Cu) and aluminum (Al). The collimator lens 26 turns the light output from the light emitting device 22 into a parallel light. The collimator lens 26 is a ball lens or a drum lens and is arranged such that the light emitting device 22 is located at the focal position of the collimator lens 26. The light emitted by the light emitting device 22 is converted into a parallel light by the collimator lens 26 and is incident on the irradiation unit 30.

The irradiation unit 30 includes a plurality of beam splitters 31~35 and splits the light from the light source unit 20 into a plurality of irradiation light beams and outputs the beams. The plurality of beam splitters 31~35 are arranged in the first direction (x direction). The plurality of beam splitters 31~35 are arranged to transmit, in the first direction, a portion of the light incident in the first direction and to reflect a portion of the incident light in a second direction (z direction).

The first beam splitter 31 is arranged to reflect a portion of the light from the light source unit 20 toward a first opening 45. The second beam splitter 32 is arranged adjacent to the first beam splitter 31 and reflects a portion of the light transmitted through the first beam splitter 31 toward a second opening 46. The third beam splitter 33 is arranged adjacent to the second beam splitter 32 and reflects a portion of the light transmitted through the second beam splitter 32 toward a third opening 47. The fourth beam splitter 34 is arranged adjacent to the third beam splitter 33 and reflects a portion of the light transmitted through the third beam splitter 33 toward a fourth opening 48. The fifth beam splitter 35 is arranged adjacent to the fourth beam splitter 34 and reflects a portion of the light transmitted through the fourth beam splitter 34 toward a fifth opening 49.

The plurality of beam splitters 31~35 produce irradiation light beams having intensities that are progressively smaller in the first direction by reflecting, in the second direction, a portion of the light transmitted in the first direction. For example, given that the reflectivity of the plurality of beam splitters 31~35 is 50%, the intensities of the irradiation light beams output are 50%, 25%, 13%, 6%, and 3%. Thus, the plurality of beam splitters 31~35 produce a plurality of irradiation light beams having intensities that are progressively smaller in stages.

The reflectivity of the plurality of beam splitters 31~35 may be determined in accordance with the intensities of irradiation light beams required in the test. For example, given that the reflectivity of the plurality of beam splitters 31~35 is 30%, i.e., that the transmissivity is 70%, the intensities of 30%, 21%, 15%, 10%, and 7% irradiation light beams reflected by and output from the plurality of beam splitters 31~35 are obtained. If the plurality of beam splitters have the identical reflectivity, the difference in intensity between irradiation light beams adjacent in the first direction can be reduced by reducing the reflectivity. Meanwhile, the dynamic range of the irradiation light beams can be increased by increasing the reflectivity of the beam splitters. The plurality of beam splitters 31~35 may have different values of reflectivity. In this case, it is desired that the reflectivity of each of the plurality of beam splitters 31~35 be defined such that the minimum irradiance level, maximum irradiance level, and irradiance level interval suited to the purpose are obtained. Alternatively, the irradiation unit 30 may be configured to be replaceable so that the reflectivity of the beam splitters can be changed in accordance with the purpose of a test.

Each of the plurality of beam splitters 31~35 functions as a light irradiation unit for outputting irradiation light used in the test. The plurality of light irradiation units, which correspond to the beam splitters 31~35, respectively, are configured to output irradiation light beams with different intensities in the z direction. The plurality of light irradiation units are configured such that the intensities of irradiation light beams output therefrom are progressively smaller in the x direction.

The housing 40 houses the light source unit 20, the irradiation unit 30, etc. inside. For example, the housing 40 has a substantially cuboid box shape and is molded by a material such as metal and resin. The top surface 41 of the housing 40 is provided with the user control unit 54 and the display unit 56. The bottom surface 42 is provided with the openings 43 for outputting irradiation light. The openings 43 include a first opening 45~fifth opening 49 corresponding to the plurality of beam splitters 31~35. The first opening 45~fifth opening 49 are arranged in the first direction.

The controller 50 controls light emission of the light emitting device 22 based on an input from the user control unit 54. The controller 50 causes the display unit 56 to display information for configuring the irradiation conditions such as emission intensity and lighting duration of the light emitting device 22, and receives the configuration of these conditions via an input in the user control unit 54. The controller 50 may maintain a plurality of test modes and irradiation conditions corresponding to the test modes. The controller 50 may control the light emitting device 22 to output an illumination light of an irradiation condition corresponding to a designated test mode, by causing the display unit 56 to display a list of a plurality of test modes and acknowledging an input from the user control unit 54 for designation of a test mode.

The power supply 52 supplies electric power to the light emitting device 22, the controller 50, etc. The power supply 52 includes a battery housed inside the housing 40. For example, the power supply 52 may comprises a rechargeable battery such as a lithium ion battery. The power supply 52 includes a power supply terminal for charging the rechargeable battery and is configured to charge the rechargeable battery via an AC adapter connected to the power supply terminal. The power supply may include a primary battery or a dry cell, which is a secondary battery. In this case, the housing 40 may be provided with a battery holder for holding the dry cell.

The user control unit 54 is used to start or end irradiation by the test device 10 and to configure the irradiation condition of the test device 10. The display unit 56 comprises, for example, a liquid crystal display and displays the operating condition of the test device 10, the irradiation condition configured, etc. The user control unit 54 may comprise a switch, button, etc. provided at positions different from that of the display unit 56. Alternatively, the user control unit 54 may be configured as a touch panel integrated with the display unit 56.

A description will now be given of a method of using the test device 10. First, the irradiation condition is determined by configuring a test mode suited to the details of the test. Subsequently, the test device 10 is located such that the bottom surface 42 is in intimate contact with the skin irradiated. In the case of testing the skin in the upper arm or thigh, the arm or leg and the test device 10 are secured to each other by a retainer such as a belt, an adhesive skin patch, etc. so that the position of the test device 10 is not shifted during irradiation. If a small gap is created between the test device and the skin, a cover shielding ultraviolet light (e.g., cloth) may be attached to cover both the test device 10 and the subject of irradiation so that the ultraviolet light is not leaked outside. Once the test device 10 is fixed, irradiation by a test light is started. Irradiation is automatically stopped when a predefined time has elapsed since the start of irradiation. After irradiation is stopped, the test device 10 is removed. The skin irradiated by the test device 10 is diagnosed after a predetermined period of time (e.g., 1~2 days after) by a doctor for presence of erythema, and MED, MRD, or MPD is identified.

According to the embodiment, the irradiation unit 30 can produce a plurality of irradiation light beams having different intensities and irradiate the skin at the same time. Therefore, as compared with the method of radiating a test light and changing the irradiation condition on individual occasions, the irradiation time can be reduced and the effort of the test staff can be reduced. This can reduce the burden on doctors and patients in the test.

According to this embodiment, the light emitting device 22 such as an LED is used as the light source in the light source unit 20 and the irradiation unit 30, the power supply 52, etc. are housed inside the housing 40 in an integrated manner. Therefore, the size of the test device 10 can be reduced. In particular, the size of the device can be significantly reduced as compared with the case of using an excimer lamp or a fluorescent lamp, which is generally used as a light source in medical ultraviolet irradiation devices. Photosensitivity tests can be easily performed even in facilities where it has been impossible to install a large sized photosensitivity test device due to space constraints.

According to this embodiment, the test device 10 is small in size so that it is possible to perform a test by placing the test device 10 in intimate contact with the upper arm or thigh. Therefore, preparation such as letting the patient lie on a bed and exposing the back of the patient for the test is not necessary any longer. Further, the patient with the test device fixed to the upper arm can move even while the patient is being irradiated by a test light and so can move outside the clinic. Since hazardous ultraviolet light is not leaked outside the test device 10, irradiation by a test light can be performed by using, for example, a waiting room instead of a bedded private room (medical examination room) where there are no other patients or staff. In further accordance with the embodiment, it is not necessary to prepare a closed space dedicated to the purpose of performing light irradiation. This can reduce the burden on doctors and patients in the test. Since a medical examination room need not be occupied during a test, the waiting time for next patients can be reduced.

According to this embodiment, it is possible to perform a test by placing the test device 10 in intimate contact with the skin subject to the test. Therefore, the skin facing the openings 43 can be irradiated a test light with an irradiance level as designed. In the related art test method using a porous plate, a gap created between the porous plate and the skin causes the test light to be leaked around the window hole, irradiating the skin in a portion corresponding to other window holes, with the result that the target skin is not irradiated with an accurate light dose and accurate test results cannot be obtained. Meanwhile, according to the embodiment, a small sized test device 10 is placed in intimate contact with the skin for use so that the test light output from each of the plurality of openings 45~49 is prevented from being leaked to adjacent regions. This can enhance the accuracy and safety of the test.

(Variation 1)

Figure 4:
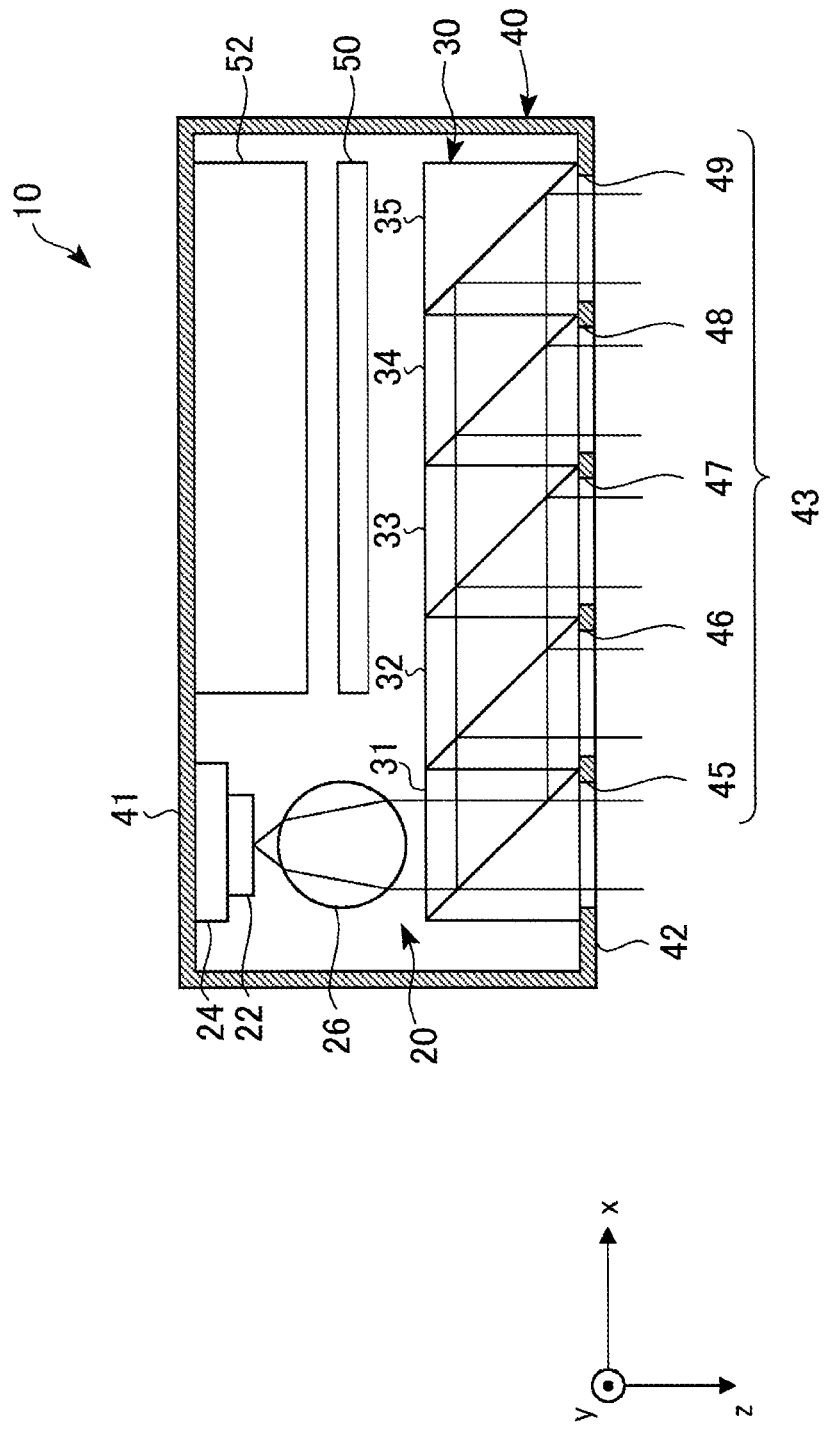
FIG. 4 schematically shows a configuration of a test device according to a variation.

FIG. 4 schematically shows a configuration of the test device 10 according to a variation. The variation differs from the embodiment described above in that the light source unit and the irradiation unit 30 are arranged in the second direction (z direction). The following description of the variation highlights the difference from the embodiment described above.

The light source unit 20 is arranged such that the light output from the light emitting device 22 and turned into a parallel light by the collimator lens 26 is incident on the first beam splitter 31 in the z direction. The light emitting device 22, the collimator lens 26, and the first beam splitter 31 are arranged in a single line in the z direction as illustrated. Further, the substrate 24 on which the light emitting device 22 is mounted is fixed to a member constituting the top surface 41 of the housing 40.

The irradiation unit 30 is configured such that the plurality of beam splitters 31~35 are arranged in the x direction. The plurality of beam splitters 31~35 are fixed to a member constituting the bottom surface 42 of the housing 40. The first beam splitter 31 is arranged to transmit a portion of the light incident from the light source unit 20 toward the first opening in the z direction and reflect another portion toward the second beam splitter 32 in the x direction. The second beam splitter 32, the third beam splitter 33, the fourth beam splitter 34, and the fifth beam splitter 35 are arranged to reflect a portion of the light from the adjacent beam splitter toward the corresponding openings 46~49 in the z direction.

The controller 50 and the power supply 52 are arranged to be in alignment with the irradiation unit 30 in the z direction and are provided at positions between the second beam splitter 32, the third beam splitter 33, the fourth beam splitter 34, the fifth beam splitter 35 and a member constituting the top surface 41 of the housing 40.

According to the variation, the irradiation unit 30 is provided toward the bottom surface 42 and the components other than the irradiation unit 30, including the light source unit 20, the controller 50, and the power supply 52 are provided toward the top surface 41. Therefore, the area of the bottom surface 42 can be reduced as compared with the embodiment described above. Hardly any skin on a human body is planar and portions that can be approximated by planes are also limited. Therefore, if the area of the bottom surface 42 is large, it would be difficult to place the test device 10 in intimate contact with the skin and the practicality of the test device 10 is impaired. According to the variation, the area of the bottom surface 42 can be reduced and intimate contact of the test device 10 with the patient's skin is facilitated so that the convenience of the test device 10 can be enhanced. Intimate contact of the test device 10 with the skin prevents leakage of light to a space around and prevents positional displacement of the device so that the accuracy and safety of tests can be enhanced.

(Variation 2)

Figure 5:
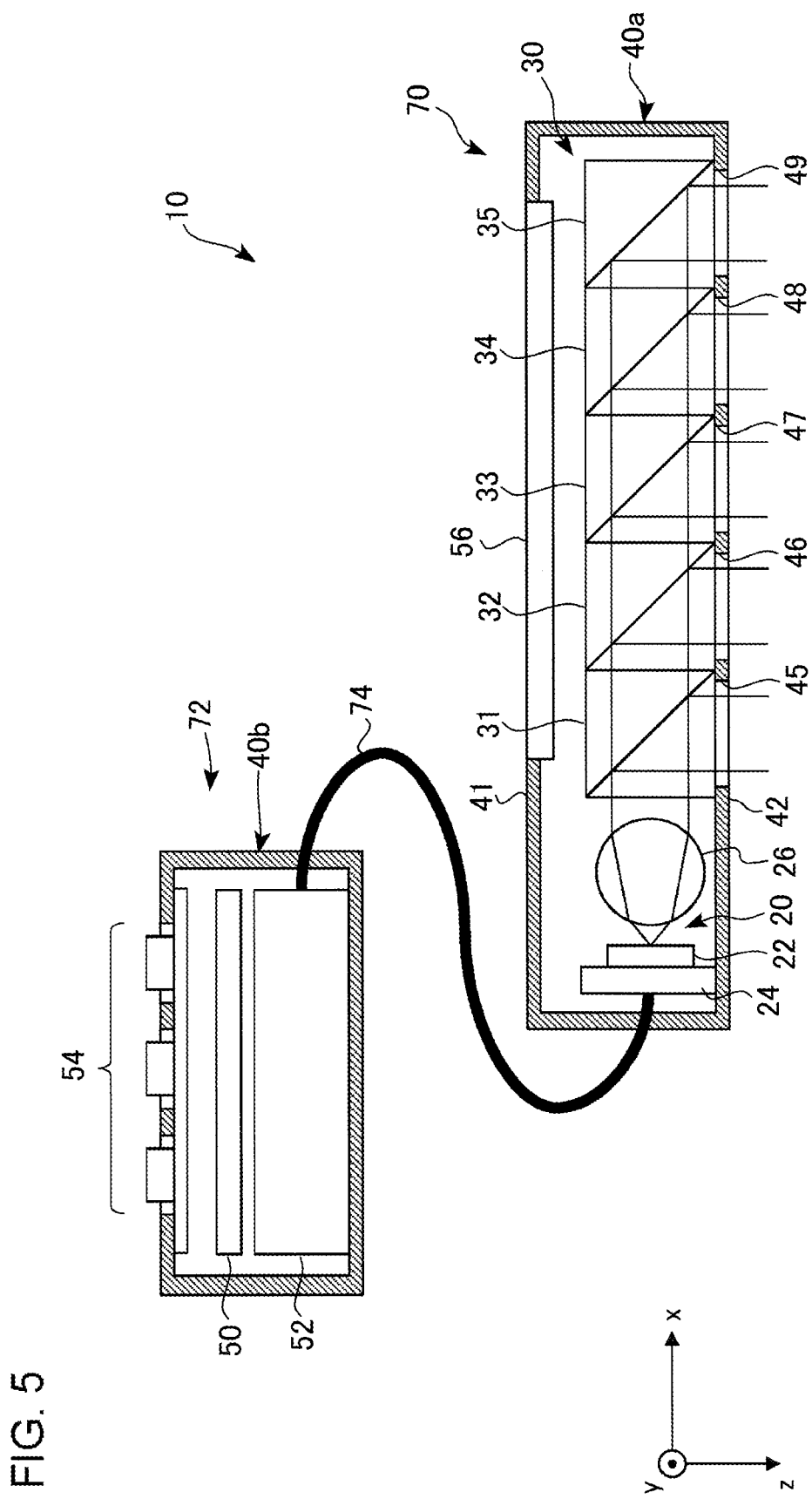
FIG. 5 schematically shows a configuration of a test device according to a variation.

FIG. 5 schematically shows a configuration of the test device 10 according to a variation. The variation differs from the embodiment described above in that a head unit 70 and a main unit 72 are separated, the head unit 70 being provided with the light source unit 20 and the irradiation unit 30, and the main unit 72 being provided with the controller 50 and the power supply 52. The following description of the variation highlights the difference from the embodiment described above.

The test device 10 is provided with the head unit 70, the main unit 72, and a cable 74. The head unit 70 includes the light source unit 20, the irradiation unit 30, a head housing portion 40a, and the display unit 56. The main unit 72 includes a main unit housing portion 40b, the controller 50, and the user control unit 54. The head unit 70 and the main unit 72 are electrically connected by the cable 74.

According to this variation, the test device 10 is separated into the head unit 70 and the main unit 72 so that the size of the head unit 70 is reduced as compared with the test device of the embodiment described above. This can reduce the area of the bottom surface 42 in contact with the patient's skin. Therefore, this variation, like the aforementioned variation, facilitates intimate contact of the test device 10 with the patient's skin and enhances the convenience of the test device 10. Intimate contact of the test device 10 with the skin prevents leakage of light to a space around and prevents positional displacement of the device so that the accuracy and safety of tests can be enhanced.

(Variation 3)

Figure 6:
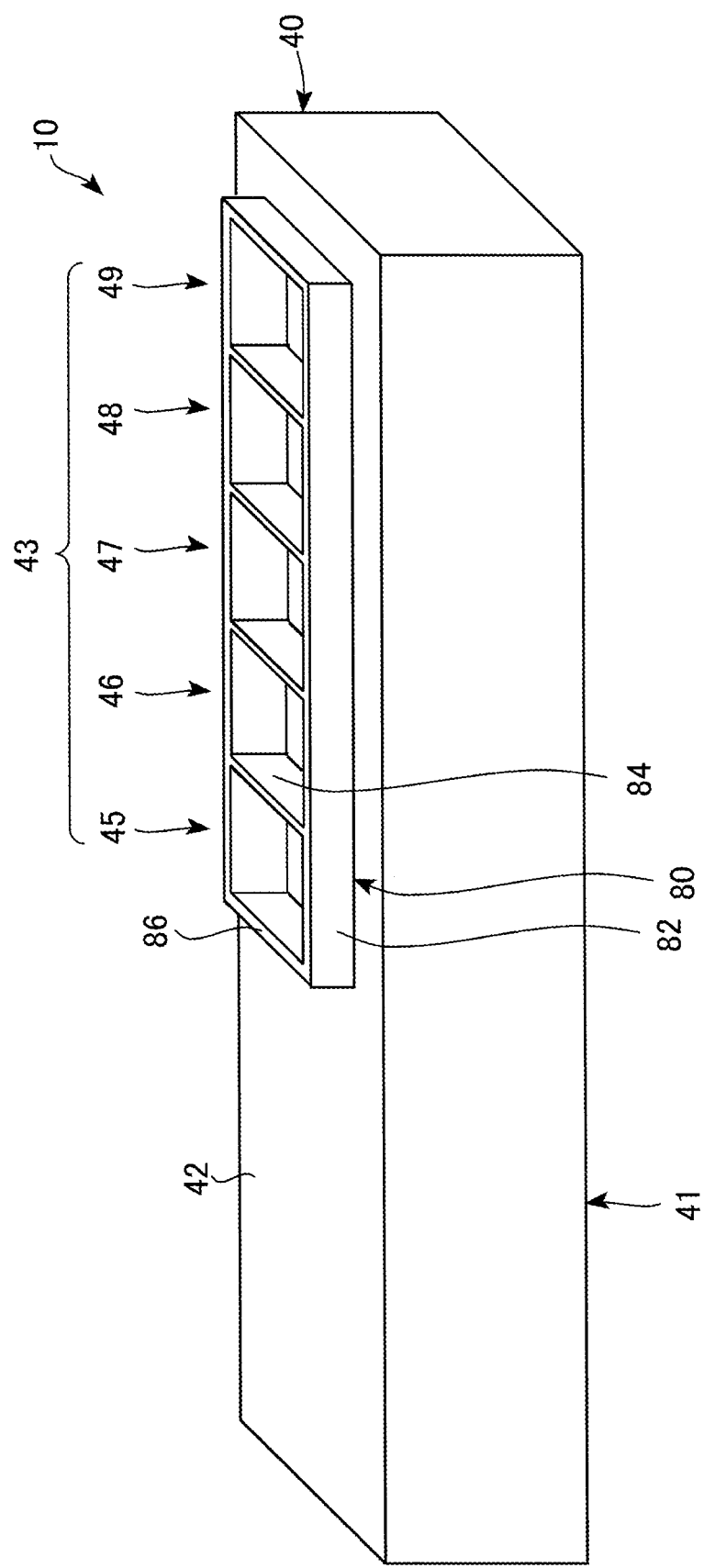
FIG. 6 schematically shows a configuration of a test device according to a variation.

FIG. 6 is a perspective schematically showing an appearance of the test device 10 according to a variation and shows a configuration of the bottom surface 42. This variation differs from the embodiment described above in that a frame body is provided to project from the bottom surface 42. The following description of the variation highlights the difference from the embodiment described above.

The housing 40 includes a frame body 80 provided on the bottom surface 42. The frame body 80 includes an outer circumferential frame 82 provided to surround the openings 43 and partition frames 84 provided to partition the plurality of openings 45~49 respectively. The frame body 80 is made of the same resin or metal material as the housing 40.

The test device 10 is used such that an end face 86 of the frame body 80 is in contact with the patient's skin. The frame body 80 ensures that the test light beams output from the plurality of openings 45~49 respectively irradiate the skin in the regions surrounded by the frame body 80 and that the test light output from each of the plurality of openings 45~49 is not leaked to adjacent regions. For example, the frame body 80 ensures that the entirety of the test light output from the first opening 45 irradiates the skin facing the first opening 45 and does not irradiate the skin facing the adjacent second opening 46.

According to the variation, the gap between the bottom surface 42 and the skin can be blocked by the frame body 80 so that the skin facing the openings 43 can be irradiated by the test light at an irradiance level as designed and hazardous ultraviolet light is prevented from being leaked around the test device 10. By preventing light rays from being leaked from the openings 45~49, the irradiance level around the openings 45~49 is prevented from becoming larger than the preset value and the irradiance level on the target skin is prevented from becoming inaccurate. This can enhance the precision of tests using the test device 10 and can enhance the safety of tests. Also, by providing the frame body 80, the area of contact with the skin can be reduced.

According to this variation, by performing a test while pressing the frame body 80 against the skin, an impression can be made around the region irradiated by the test light to serve as a mark of the region tested. The impression that serves as a mark is not displaced from the position of irradiation so that the accuracy of tests can be enhanced. Instead of making an impression mark, the end face 86 of the frame body 80 may be inked for a test so that a mark corresponding to the shape of the frame body 80 remains in the test region. Alternatively, a mark corresponding to the shape of the frame body 80 may be applied before a test to the skin subject to the test by using a non-permanent marker or a seal and the test may be performed by placing the test device 10 along the mark.

(Variation 4)

Figure 7:
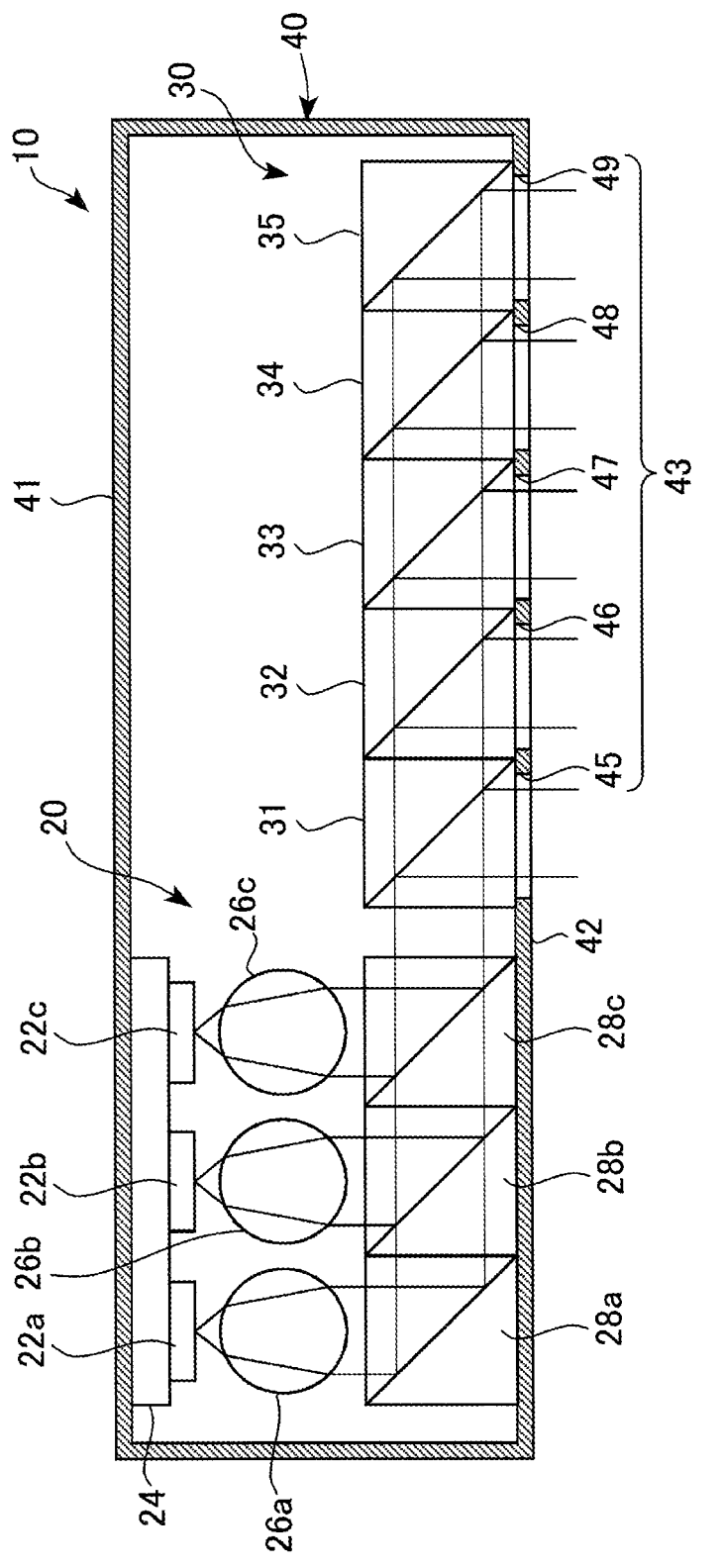
FIG. 7 schematically shows a configuration of a test device according to the variation.

FIG. 7 schematically shows a configuration of the test device 10 according to a variation. The variation differs from the embodiment described above in that the light source unit 20 includes a plurality of light emitting devices 22a, 22b, and 22c. The following description of the variation highlights the difference from the embodiment described above.

The light source unit 20 includes the plurality of light emitting devices 22a, 22b, 22c, the substrate 24, a plurality of collimator lenses 26a, 26b, 26c, and a plurality of beam combiners 28a, 28b, 28c. The light source unit 20 according to this variation is capable of producing test light beams of a wide wavelength range by combining a plurality of light emitting devices having different central wavelengths or peak wavelengths.

The plurality of light emitting devices 22a-22c are LEDs having different central wavelengths or peak wavelengths. For example, the first light emitting device 22a is an AlGaN based LED having a central wavelength or peak wavelength of 340 nm, the second light emitting device 22b is an AlGaN based or GaN based LED having a central wavelength or peak wavelength of 365 nm, and the third light emitting device 22c is a GaN based LED having a central wavelength or peak wavelength of 385 nm. By synthesizing the light of these three wavelengths, test light beams covering a UVA wavelength band of 320 nm-400 nm can be produced.

The plurality of collimator lenses 26a-26c convert the light output from the corresponding light emitting devices 22a-22c into a parallel light. The plurality of beam combiners 28a-28c synthesize the parallel light output from the collimator lenses 26a-26c. For example, each of the plurality of beam combiners 28a-28c may be an optical element such as a beam splitter.

The first beam combiner 28a reflects the parallel light from the first collimator lens 26a in the first direction (x direction). The second beam combiner 28b reflects the parallel light from the second collimator lens 26b in the first direction and transmits the parallel light from the first beam combiner 28a in the first direction. The third beam combiner 28c reflects the parallel light from the third collimator lens 26c in the first direction and transmits the parallel light from the second beam combiner 28b in the first direction. The parallel light from the third beam combiner 28c is incident on the irradiation unit 30. In this way, the synthesized light derived from synthesizing the light from the plurality of light emitting devices 22a-22c can be provided to the irradiation unit 30. The irradiation unit 30 splits the synthesized light output from the light source unit 20 into a plurality of irradiation light beams and outputs the irradiation light beams thus split.

According to this variation, the synthesized light produced by synthesizing the light from the plurality of light emitting devices 22a-22c can be used as the test light. In this way, even in the case of a test that requires a wider wavelength band than a wavelength band that a single light emitting device is capable of outputting, a test light suited to the test can be provided. In particular, this variation enables tests using UVA waves characterized by wider wavelength band than tests using UVB waves. Thus, according to this variation, the same advantage from the embodiment described above is available in photosensitivity tests that use a test light of a wide wavelength band such as UVA waves.

This variation provides a test light of wavelength characteristics equivalent or similar to those of irradiation devices that have been used in the related art for photosensitivity tests or light treatment. The output light of a light emitting device such as an LED has a narrow wavelength band and is monochromatic, which are in contrast to the wavelength characteristics of irradiation devices that have been used in the related art. For this reason, the related art knowledge in photosensitivity tests or light treatment may not be utilized directly if a light emitting device is used alone due to the difference in wavelength characteristics. For example, PUVA therapy that uses psoralen having a phototoxic property assumes using UVA waves so that tests that use UVA waves are indispensable. According to this variation, a test device small in size and having wavelength characteristics equivalent to those of the related art irradiation devices can be provided by combining a plurality of light emitting devices. It is therefore possible to perform suitable and highly safe tests based on the related art knowledge. In further accordance with this variation, MED or MPD can be determined more accurately when performing a treatment using the related art irradiation device based on the test result of the test device 10.

(Variation 5)

Figure 8:
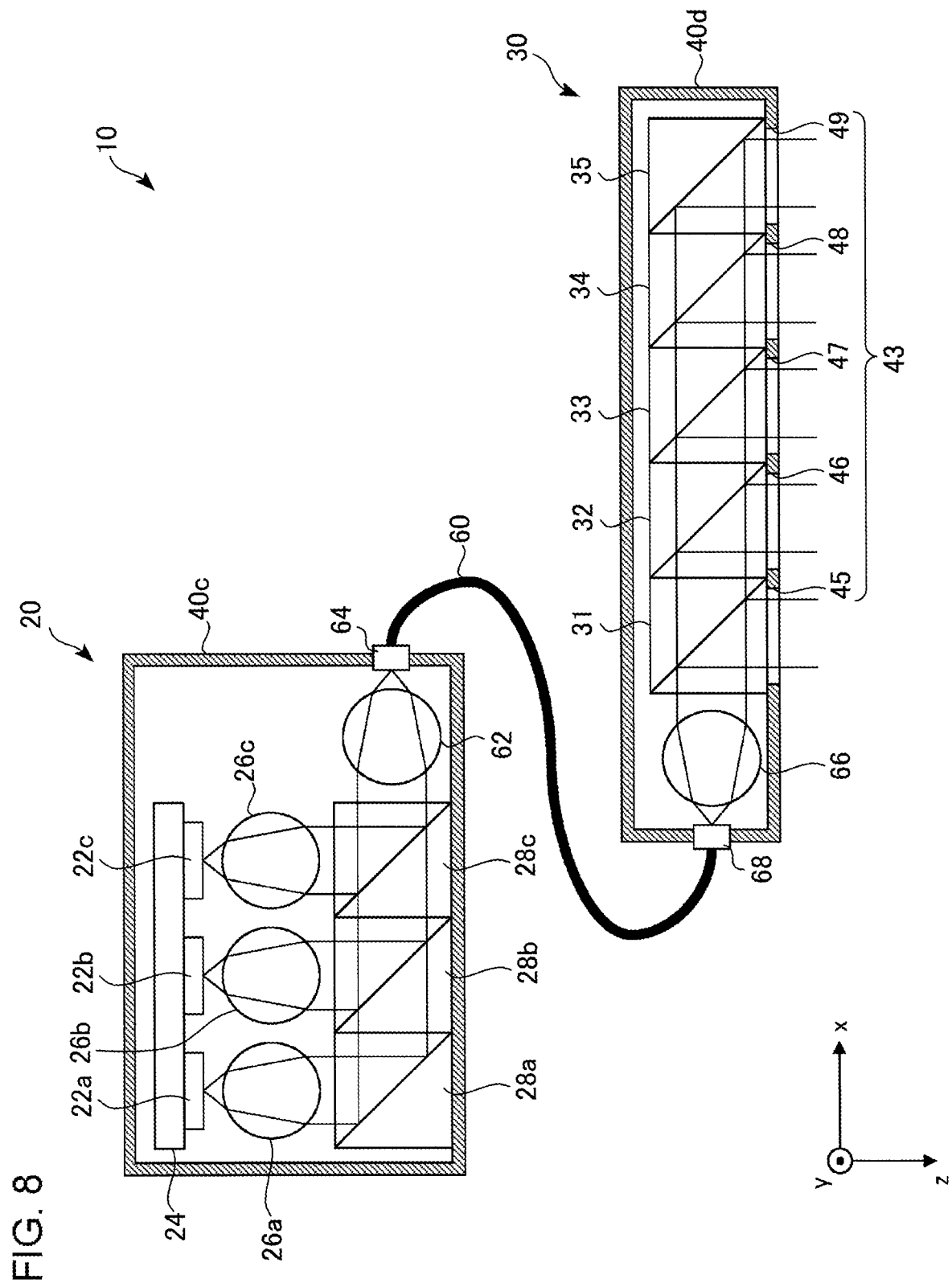
FIG. 8 schematically shows a configuration of a test device according to this variation.

FIG. 8 schematically shows a configuration of the test device 10 according to a variation. The variation differs from the variations described above in that the light source unit 20 and the irradiation unit 30 are provided in separate housings and the light source unit 20 and the irradiation unit 30 are connected by an optical fiber 60. The following description of the variation highlights the difference from the embodiment and variations described above.

The light source unit 20 includes the plurality of light emitting devices 22a, 22b, 22c, the substrate 24, the plurality of collimator lenses 26a, 26b, 26c, and the plurality of beam combiners 28a, 28b, 28c. The light source unit 20 further includes a light source side coupling lens 62 and a light source side connector 64. The light source unit 20 is housed in a light source unit housing 40c.

The light source side connector 64 is an optical connector to which the input end of the optical fiber 60 is coupled. The light source side coupling lens 62 causes causes the synthesized light output from the third beam combiner 28c to be incident on the optical fiber 60 coupled to the light source side connector 64. The light source side coupling lens 62 is a ball lens or a drum lens and is arranged such that the light source side connector 64 is located at the focal position of the light source side coupling lens 62.

The irradiation unit 30 includes the plurality of beam splitters 31~35. The irradiation unit 30 further includes an irradiation side coupling lens 66 and an irradiation side connector 68. The irradiation unit 30 is housed in an irradiation unit housing 40d. The irradiation unit housing 40d is provided with openings 43 for transmitting the irradiation light reflected and output by the plurality of beam splitters 31~35.

The irradiation side connector 68 is an optical connector to which the output end of the optical fiber 60 is coupled. The irradiation side coupling lens 66 converts the light emitted from the optical fiber 60 coupled to the irradiation side connector 68 into a parallel light. The irradiation side coupling lens 66 is a ball lens or a drum lens and is arranged such that the irradiation side connector 68 is located at the focal position of the irradiation side coupling lens 66. The parallel light from the irradiation side coupling lens 66 is incident on the first beam splitter 31.

According to this variation, the light source unit 20 and the irradiation unit 30 are separate so that the portion placed in contact with the patient's skin for use can be further reduced in size as compared with the case where the light source unit 20 and the irradiation unit 30 are integrated. Therefore, the burden experienced by the patient when the irradiation unit 30 is fixed to the upper arm or thigh for use can be reduced.

According to this variation, the light source unit 20 and the irradiation unit 30 are separate so that a plurality of types light source units and irradiation units having different characteristics can be combined for use. For example, when it is desired to change the wavelength of the irradiation light, a common irradiation unit 30 can continue to be used for the test merely by switching to the light source unit 20 having a different output wavelength. When it is desired to change an intensity difference in the irradiation light, a common light source unit 20 can continue to be used for a test merely by switching to the irradiation unit 30 with a different reflectivity of the beam splitter. A light source device other than a light emitting device like an LED, and, more particularly, a light source device that uses a lamp or the like may be used as the light source unit.

Second Embodiment

Figure 9:
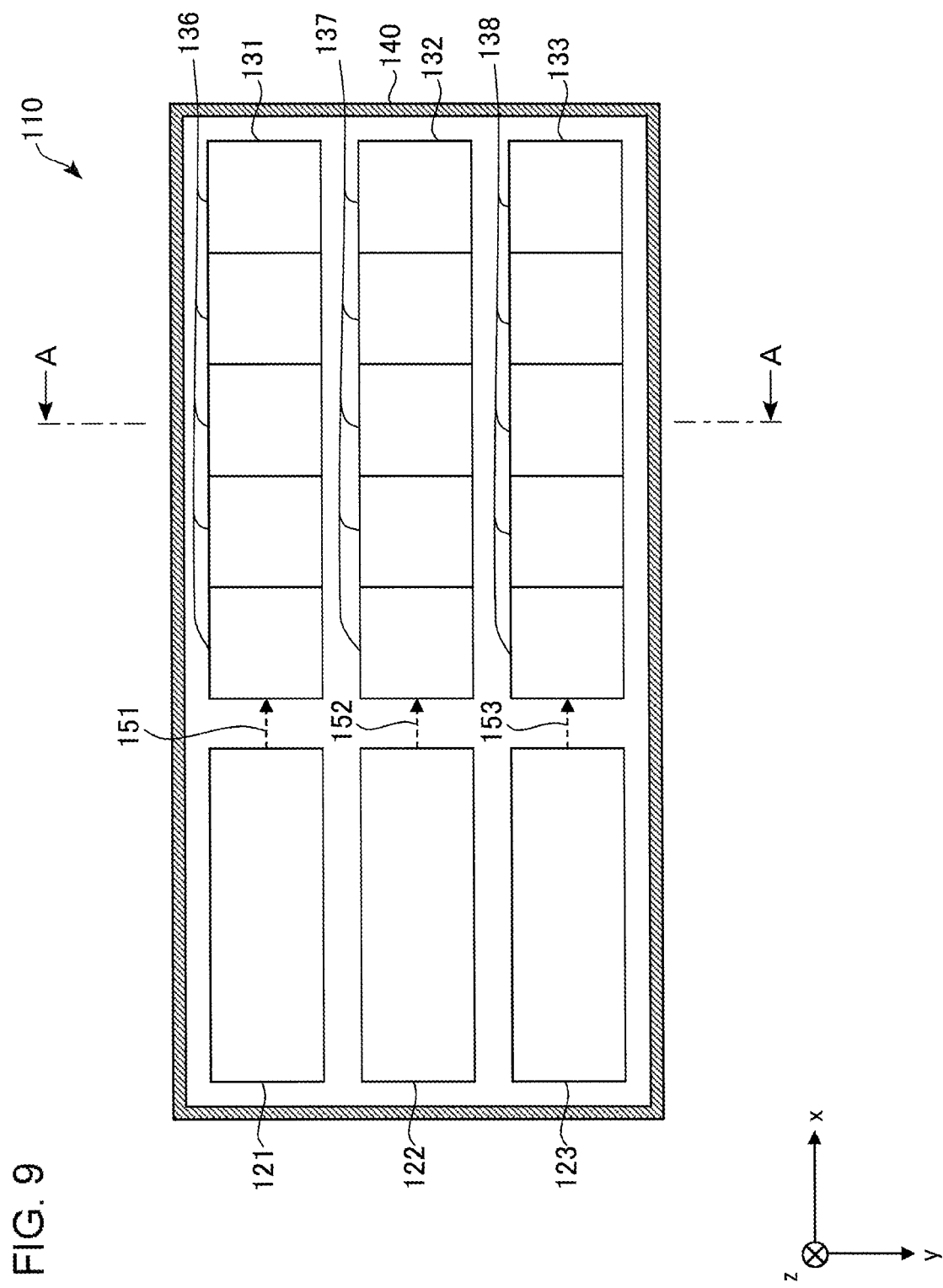
FIG. 9 schematically shows a configuration of a test device according to the second embodiment.

FIG. 9 schematically shows a configuration of a test device 110 according to the second embodiment. FIG. 10 shows an A-A cross section of FIG. 9, and FIG. 9 corresponds to a B-B cross section of FIG. 10. The second embodiment differs from the embodiment described above in that the test device 110 includes a plurality of light source units 121, 122, 123 and a plurality of irradiation units 131, 132, 133. The following description of the variation highlights the difference from the embodiment and variations described above.

The plurality of light source units 121~123 has a configuration similar to that of the light source unit 20 according to the embodiment or variations described above but are configured to output light of different wavelength bands. The first light source unit 121 is configured to output a first test light 151 including ultraviolet light of a first wavelength band. More specifically, the first light source unit 121 is configured to output UVB waves of a 290 nm-320 nm wavelength band. For example, the first light source unit 121 includes an LED having a central wavelength or peak wavelength of about 350 nm as a light emitting device and is configured similarly as the light source unit 20 shown in FIG. 1.

The second light source unit 122 is configured to output a second test light 152 including ultraviolet light of a second wavelength band more toward the long-wavelength side than the first wavelength band. More specifically, the second light source unit 122 is configured to output UVA waves of a 320 nm-400 nm wavelength band. For example, the second light source unit 122 includes three LEDs having central wavelengths or peak wavelengths of 340 nm, 365 nm, and 385 nm as light emitting devices and is configured similarly as the light source unit 20 shown in FIG. 7.

The third light source unit 123 is configured to output a third test light 153 including visible light. More specifically, the third light source unit 123 is configured to output light in a visible light range of a wavelength of 400 nm or longer. For example, the third light source unit 123 includes three LEDs outputting red, green, and blue light, respectively, as light emitting devices and is configured similarly as the light source unit 20 shown in FIG. 7. In this case, the third light source unit 123 outputs a pseudo white light. A light emitting device such as an incandescent bulb capable of outputting light having a continuous spectrum over a visible light range can be used as a light emitting device in the third light source unit 123. In this case, it is desired that an infrared (IR) cut filter for blocking heat waves emitted by the incandescent bulb be provided in the third light source unit 123.

Each of the plurality of irradiation units 131~133 is configured similarly as the irradiation unit 30 according to the embodiment or variations. The first irradiation unit 131 includes a plurality of beam splitters 136 arranged in the first direction (x direction). A first test light 151 from the first light source unit 121 is incident on the first irradiation unit 131. The first test light 151 is split into a plurality of first irradiation light beams 156 by the plurality of beam splitters 136 of the first irradiation unit 131. The plurality of first irradiation light beams 156 are output in the second direction (z direction) from first openings 143 of a housing 140.

The second irradiation unit 132 includes a plurality of beam splitters 137 arranged in the first direction. A second test light 152 from the second light source unit 122 is incident on the second irradiation unit 132. The second test light 152 is split into a plurality of second irradiation light beams 157 by the plurality of beam splitters 137 of the second light source unit 122. The plurality of second irradiation light beams 157 are output in the second direction from second openings 144 of the housing 140.

The third irradiation unit 133 includes a plurality of beam splitters 138 arranged in the first direction. A third test light 153 from the third light source unit 123 is incident on the third irradiation unit 133. The third test light 153 is split into a plurality of third irradiation light beams 158 by the plurality of beam splitters 138 of the third light source unit 123. The plurality of third irradiation light beams 158 are output in the second direction from third openings 145 of the housing 140.

The plurality of light source units 121~123 are arranged in a third direction (y direction) intersecting both the first direction and the second direction. Similarly, the plurality of irradiation units 131~133 are arranged in the third direction. The plurality of light source units 121~123 and the plurality of irradiation units 131~133 are housed inside the housing 140.

Figure 11:
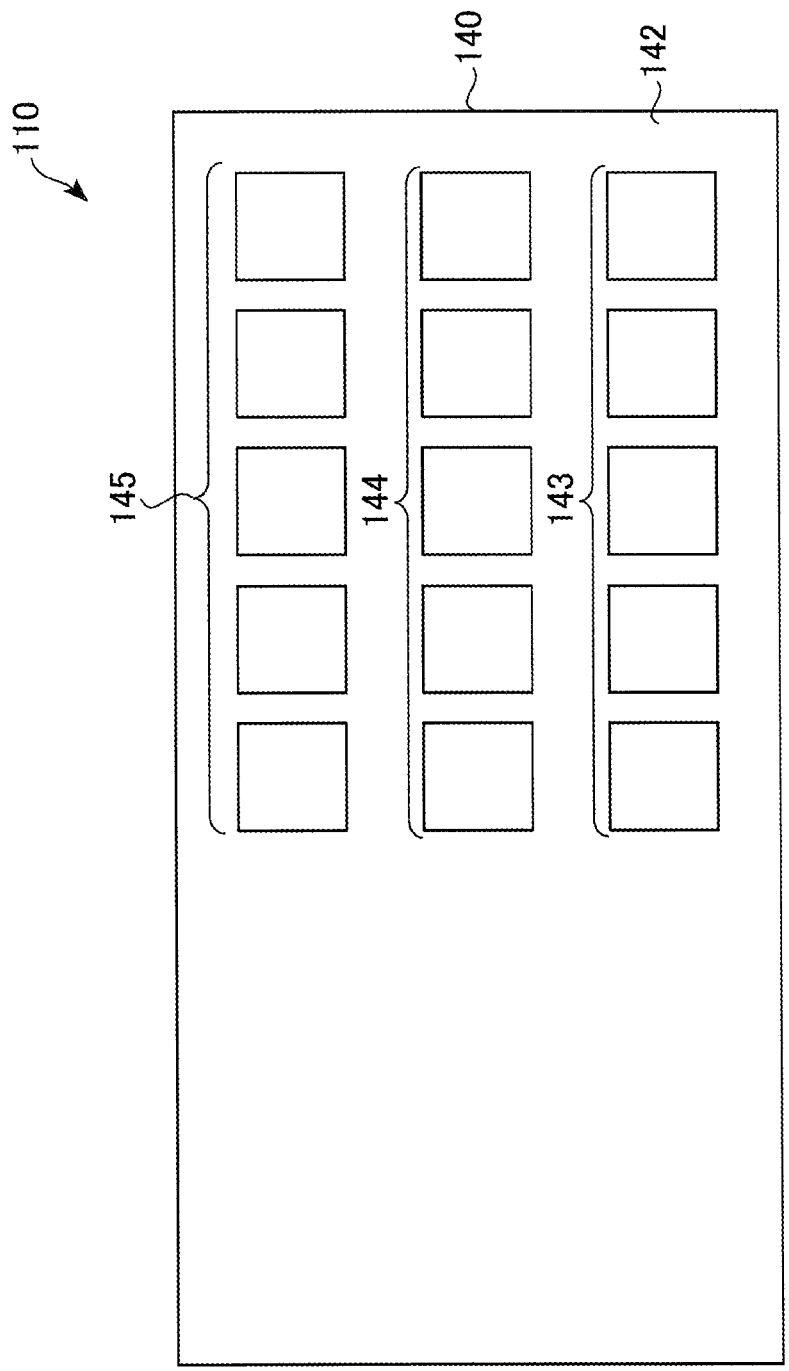
FIG. 11 is a bottom view schematically showing a configuration of the test device of FIG. 9.

FIG. 11 shows the test device 110 as viewed from the bottom surface 142. As shown in the figure, the first openings 143 include a plurality of openings arranged in the first direction (x direction) in alignment with the plurality of beam splitters 136 of the first irradiation unit 131. Similarly, the second openings 144 include a plurality of openings arranged in the first direction in alignment with the plurality of beam splitters 137 of the second irradiation unit 132. The third openings 145 include a plurality of openings arranged in the first direction in alignment with the plurality of beam splitters 138 of the third irradiation unit 133. The first openings 143, the second openings 144, and the third openings 145 are arranged in the third direction (y direction). Therefore, the plurality of openings provided on the bottom surface 142 of the housing 140 are arranged in the x direction and in the z direction in a matrix.

With the above configuration, the test device 110 includes a plurality of beam splitters arranged in the x direction and in the y direction in a matrix. Since each beam splitter functions as a light irradiation unit, it can be said that the test device 110 has a plurality of light irradiation units arranged in a matrix or an array. Each of the plurality of light irradiation units outputs irradiation light beams that differ in at least one of wavelength characteristics and intensity in the second direction (z direction).

According to this embodiment, each of the test light beams of three wavelength bands used in photosensitivity tests can be split into a plurality of irradiation light beams having different intensities to irradiate the skin at the same time. In photosensitivity tests, three wavelength bands of light including UVB waves, UVA waves, and visible light are generally used. The minimum irradiance level inducing a reaction on the skin in response to the light of the respective wavelength band is determined. According to this embodiment, the three wavelength bands of light can be radiated at the same time for tests so that the test time can be reduced as compared with a case of radiating the light of respective wavelength band individually. This can reduce the burden on doctors and patients in the test. The burden on doctors and patients can also be reduced in tests performed before light treatment to measure MED or MPD.

Third Embodiment

Figure 12:
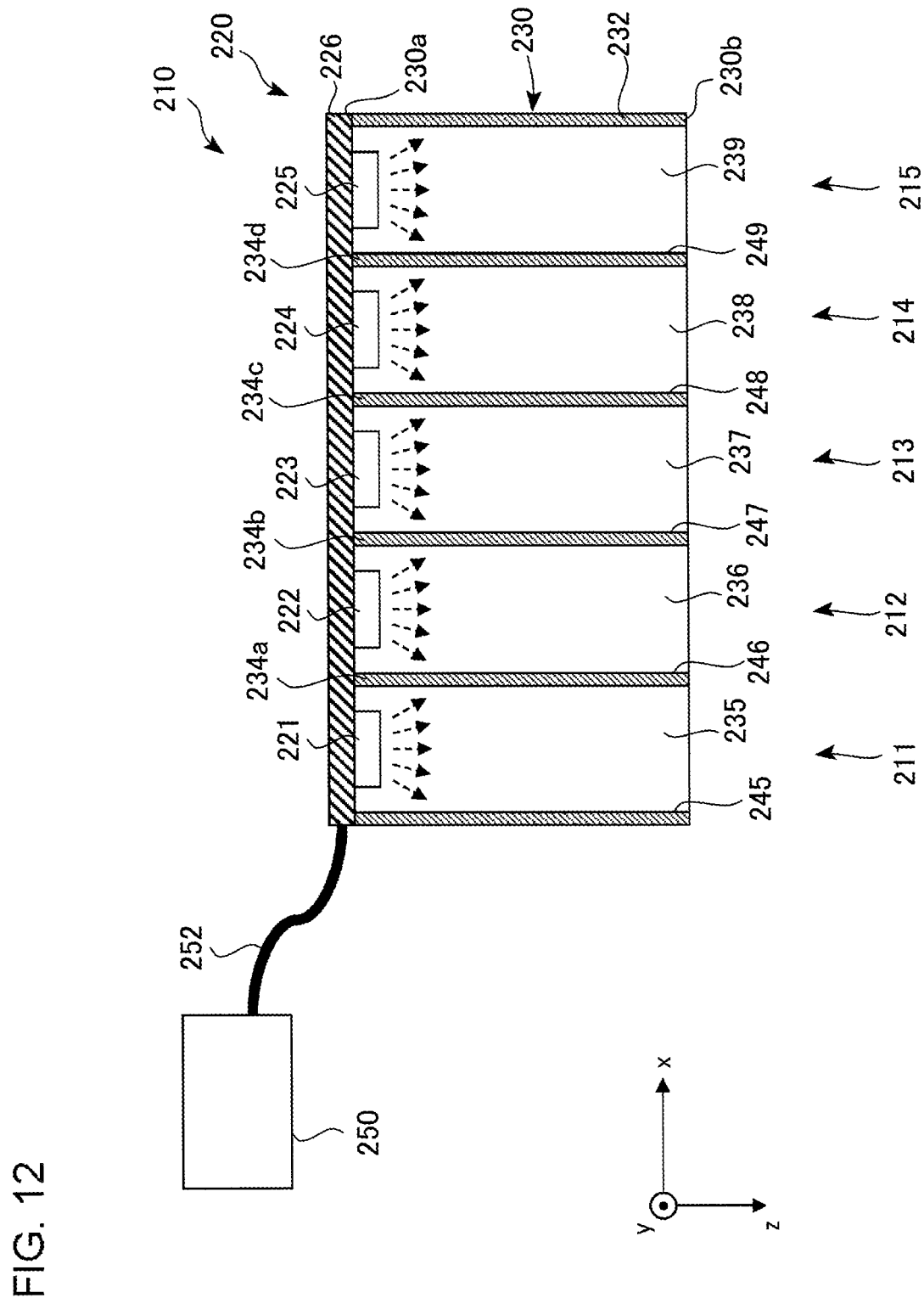
FIG. 12 schematically shows a configuration of a test device according to the third embodiment.
Figure 13:
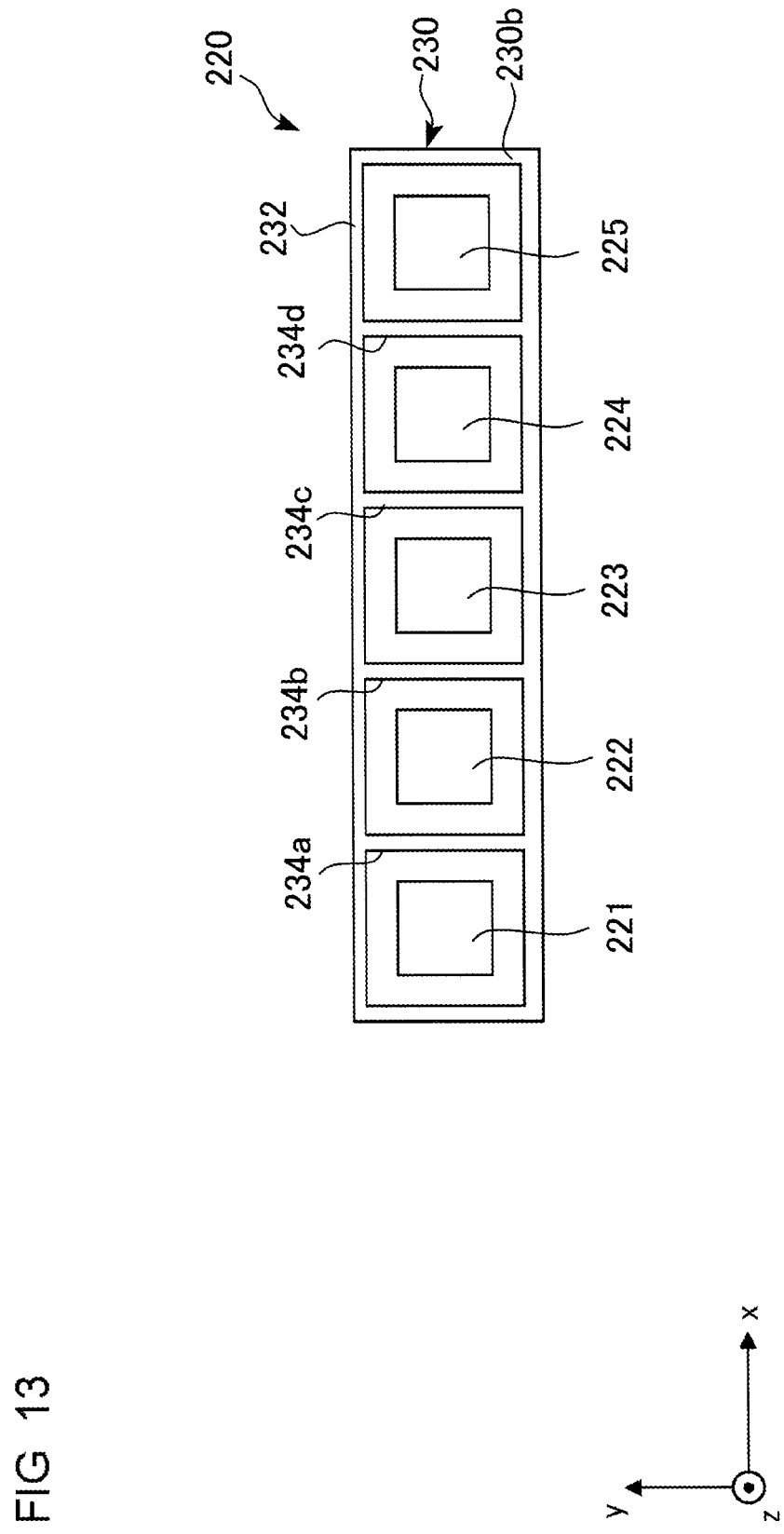
FIG. 13 is a bottom view showing a configuration of the irradiation unit of FIG. 12.

FIG. 12 schematically shows a configuration of a test device 210 according to the third embodiment. FIG. 13 shows a configuration of the irradiation unit 220 of FIG. 12 as viewed from a lower end face 230b. The test device 210 is provided with an irradiation unit 220, a control unit 250, and a cable 252. The irradiation unit 220 is provided with a plurality of light emitting devices 221, 222, 223, 224, 225, a substrate 226, and a housing 230. This embodiment differs from the embodiments described above in that the plurality of light emitting devices 221~225 and the housing 230 constitute a plurality of light irradiation units 211, 212, 213, 214, 215. The following description of the variation highlights the difference from the embodiments and variations described above.

The plurality of light emitting devices 221~225 are arranged in the first direction (x direction) and mounted on the substrate 226. Each of the plurality of light emitting devices 221~225 outputs light in the (second direction (z direction) The plurality of light emitting devices 221~225 may have the same wavelength characteristics or different wavelength characteristics.

The housing 230 includes an outer frame plate 232, and partition plates 234a, 234b, 234c, 234d. The housing 230 is made of a metal material or a resin material. It is preferable that the housing 230 be made of a material having a high ultraviolet reflectivity. For example, the housing 230 is made from an aluminum plate, or a fluoroplastic plate member containing perfluoroalkoxyalkane (PFA), polytetrafluoroethylene (PTFE), etc. Alternatively, the base of the housing 230 may be made of a material other than those listed above and the inner surface thereof may be coated with a material having a high ultraviolet reflectivity.

The outer frame plate 232 is provided to surround the outer circumference of the plurality of light emitting devices 221~225 arranged in the first direction (x direction9 and extend in the second direction (z direction). The outer frame plate 232 has the shape of a hollow rectangular tube having a rectangular bottom surface. The plurality of partition plates 234a~234d are provided to partition the space surrounded by the outer frame plate 232 into regions occupied by the plurality of light emitting devices 221~225 and extend in the z direction. The top end face 230a of the housing 230 is mounted to the substrate 226. The lower end face 230b of the housing 230 is provided with a plurality of openings 245~249.

The housing 230 forms a plurality of light guiding paths 235~239. The first light guiding path 235 is a light guiding path corresponding to the first light emitting device 221 and is partitioned by the outer frame plate 232 and the first partition plate 234a provided between the first light emitting device 221 and the second light emitting device 222. The first light guiding path 235 guides the test light output from the first light emitting device 221 to the first opening 245. The first light guiding path 235 ensures uniform intensity distribution of the irradiation light output from the first opening 245 by causing the output light from the first light emitting device 221 to be reflected by the inner wall of the housing 230 and travel in the second direction (z direction).

Each of the second light guiding path 236, the third light guiding path 237, the fourth light guiding path 238, and the fifth light guiding path 239 is configured similarly as the first light guiding path 235. The second light guiding path 236 is a light guiding path corresponding to the second light emitting device 222 and is partitioned by the outer frame plate 232, the first partition plate 234a, and the second partition plate 234b provided between the second light emitting device 222 and the third light emitting device 223. The third light guiding path 237 is a light guiding path corresponding to the third light emitting device 223 and is partitioned by the outer frame plate 232, the second partition plate 234b, and the third partition plate 234c provided between the third light emitting device 223 and the fourth light emitting device 224. The fourth light guiding path 238 is a light guiding path corresponding to the fourth light emitting device 224 and is partitioned by the outer frame plate 232, the third partition plate 234c, and the fourth partition plate 234d provided between the fourth light emitting device 224 and the fifth light emitting device 225. The first light guiding path 235 is a light guiding path corresponding to the first light emitting device 221 and is partitioned by the outer frame plate 232 and the first partition plate 234a provided between the first light emitting device 221 and the second light emitting device 222.

Each of the second light guiding path 236, the third light guiding path 237, the fourth light guiding path 238, and the fifth light guiding path 239 functions similarly as the first light guiding path 235. The second light guiding path 236 converts the test light output from the second light emitting device 222 into a uniform irradiation light and causes the uniform light to be output from the second opening 246. The third light guiding path 237 converts the test light output from the third light emitting device 223 into a uniform irradiation light and causes the uniform light to be output from the third opening 247. The fourth light guiding path 238 converts the test light output from the fourth light emitting device 224 into a uniform irradiation light and causes the uniform light to be output from the fourth opening 248. The fifth light guiding path 239 converts the test light output from the fifth light emitting device 225 into a uniform irradiation light and causes the uniform light to be output from the fifth opening 249.

The irradiation unit 220 is provided with the plurality of light irradiation units 211~215. The first light irradiation unit 211 outputs an irradiation light from the first opening 245 by lighting the first light emitting device 221. The second light irradiation unit 212 outputs an irradiation light from the second opening 246 by lighting the second light emitting device 222. The third light irradiation unit 213 outputs an irradiation light from the third opening 247 by lighting the third light emitting device 223. The fourth light irradiation unit 214 outputs an irradiation light from the fourth opening 248 by lighting the fourth light emitting device 224. The fifth light irradiation unit 215 outputs an irradiation light from the fifth opening 249 by lighting the fifth light emitting device 225.

The control unit 250 controls the operation of the plurality of light emitting devices 221~225. The control unit 250 regulates the emission intensity of the light emitting devices such that a plurality of types of irradiation light suited to the details of tests sought to be performed are output. For example, the control unit 250 ensures that the intensities of the irradiation light beams output by the plurality of light irradiation units 211~215 are progressively smaller in the first direction (x direction) by lighting the plurality of light emitting devices 221~225 such that the emission intensity is progressively smaller in the first direction (x direction).

According to this embodiment, a plurality of irradiation light beams having different intensities required for photosensitivity tests can be radiated at the same time by ensuring different emission intensities of the plurality of light emitting devices 221~225. By using LEDs having different wavelength characteristics as the plurality of light emitting devices 221~225, a plurality of irradiation light beams having different wavelength bands required for photosensitivity tests can be radiated at the same time. Thus, like the embodiments and variations described above, this embodiment can reduce the irradiation time and the effort of the test staff and also can reduce the burden on doctors and patients in the test, as compared with the method of radiating a test light and changing the irradiation condition on individual occasions.

According to this embodiment, each of the output light beams of the plurality of light emitting devices 221~225 is output via the housing 230 so that the irradiation light with an even intensity distribution can be radiated to the skin by using a simple structure. Evenness of intensity distribution of the irradiation light can prevent localized intense irradiation due to uneven irradiation that may cause inflammation, or prevent diagnosis from becoming difficult due to failure to radiate light of an intended intensity. Thus, according to this embodiment, the safety and reliability of photosensitivity tests can be enhanced.

According to this embodiment, the device can be used such that the skin subject to irradiation is placed in contact with the lower end face 230b of the housing 230. Therefore, leakage of irradiation light is prevented and the skin in a designated region facing each irradiation unit can be irradiated by a test light at an intended irradiance level. Further, by using the housing 230 similarly as the frame body 80 described above, a tested region can be marked. Thus, according to the test device 210, the precision and safety of tests can be enhanced.

It should be noted that one or a plurality of light emitting devices may be included in each of the light irradiation units 211~215. For example, by providing a plurality of light emitting devices having different wavelength characteristics in the first light irradiation unit 211, an irradiation light having a wide wavelength band such as UVA waves can be output. Alternatively, a large number of light emitting devices having mutually different wavelength characteristics may be provided in the first light irradiation unit 211 so that visible light, UVA waves, and UVB waves can be used. Similarly, a plurality of light emitting devices may be provided in each of the other light irradiation units 212~215.

Described above is an explanation based on an exemplary embodiment. The embodiment is intended to be illustrative only and it will be obvious to those skilled in the art that various modifications to constituting elements and processes could be developed and that such modifications are also within the scope of the present invention.

In the embodiments and variations above, one irradiation unit including five beam splitters is described by way of illustration. In a further variation, the number of beam splitters included in an irradiation unit and the number of irradiation light beams split by the beam splitters may be four or smaller or six or larger.

In the embodiments and variations above, the use of three light emitting devices to realize a UVA wavelength band is described by way of illustration. In a further variation, the UVA wavelength band may be realized by combining four or more light emitting devices having different central wavelengths or peak wavelengths. Alternatively, the UVB wavelength band may be realized by combining a plurality of light emitting devices having different central wavelengths or peak wavelengths.

In the embodiments and variations above, one irradiation unit realizing one wavelength band is described by way of illustration. In a further variation, in order to allow one irradiation unit to realize a plurality of wavelength bands (e.g., visible light, UVA, and UVB wavelength bands), a plurality of types of light emitting devices necessary to cover these wavelength bands may be provided in one irradiation unit. The intensity and wavelength characteristics of the irradiation light may be changed in accordance with an input from the user control unit. This can output the irradiation light having suitable wavelength characteristics according to the detail of the test that should be performed.

In the embodiments and variations above, one opening provided for one beam splitter is described by way of illustration. In a further variation, one opening may be provided for a plurality of beam splitters. For example, instead of providing the plurality of openings 45~49 as the openings 43 in the test device 10 shown in FIG. 1, an opening elongated in the first direction (x direction) may be provided.

In the embodiments and variations above, the frame body provided to surround the irradiation light beams output from the plurality of light irradiation units individually and formed in a rectangular or lattice shape is described by way of illustration. In a further variation, the frame body may be configured in a cylindrical shape or in a rectangular tube shape having a triangular or hexagonal bottom surface.

It should be understood that the invention is not limited to the above-described embodiment, but may be modified into various forms on the basis of the spirit of the invention. Additionally, the modifications are included in the scope of the invention.

What is claimed is:

1. A test device for testing photosensitivity of a skin, the test device comprising:
   a light source unit that outputs a test light;
   an irradiation unit including a plurality of beam splitters arranged in a first direction, wherein
   the test light is split into a plurality of irradiation light beams having mutually different intensities by the plurality of beam splitters,
   the plurality of irradiation light beams are output in a second direction intersecting the first direction, the plurality of beam splitters include a front beam splitter and at least one middle beam splitter,
   the front beam splitter transmits a portion of the test light from the light source unit in the first direction and reflects another portion of the test light in the second direction,
   one of the at least one middle beam splitter disposed following to the front beam splitter or another of the at least one middle beam splitter transmits a portion of the test light transmitted through the front beam splitter or the another of the at least one middle beam splitter in the first direction, and reflects another portion of the test light transmitted through the front beam splitter or the another of the at least one middle beam splitter in the second direction, and
   the intensities of the plurality of irradiation light beams are progressively smaller in the first direction by the plurality of beam splitters.

2. The test device according to claim 1, further comprising:
   a frame body that extends in the second direction and individually surrounds the plurality of irradiation light beams output from the plurality of beam splitters respectively.

3. The test device according to claim 1, wherein
   the light source unit includes a plurality of light emitting devices having different central wavelengths or peak wavelengths, synthesizes light output from the plurality of light emitting devices, and outputs the synthesized light as the test light to the irradiation unit.

4. A test device for testing photosensitivity of a skin, the test device comprising:
   a first light source unit that outputs a first test light including ultraviolet light of a first wavelength;
   a second light source unit that outputs a second test light including ultraviolet light of a second wavelength that is longer in wavelength than the first wavelength;
   a third light source that outputs a third test light including visible light;
   a first irradiation unit including a plurality of beam splitters arranged in a first direction, and splits the first test light into a plurality of first irradiation light beams having mutually different intensities by the plurality of beam splitters and outputs the first irradiation light beams in a second direction intersecting the first direction;
   a second irradiation unit that includes a plurality of beam splitters arranged in the first direction, and splits the second test light into a plurality of second irradiation light beams having mutually different intensities and outputs the second irradiation light beams in the second direction; and
   a third irradiation unit that includes a plurality of beam splitters arranged in the first direction, and splits the third test light into a plurality of third irradiation light beams having mutually different intensities and outputs the third irradiation light beams in the second direction, wherein
   each of the plurality of beam splitters in the first, second, and third irradiation unit includes a front beam splitter and at least one middle beam splitter,
   the front beam splitter transmits a portion of a corresponding test light from a corresponding light source unit in the first direction and reflects another portion of the corresponding test light in the second direction,
   one of the at least one middle beam splitter disposed following to the front beam splitter or another of the at least middle beam splitter transmits a portion of the test light transmitted through the front beam splitter or the another of the at least middle beam splitter in the first direction, and reflects another portion of the test light transmitted through the front beam splitter or the another of the at least middle beam splitter in the second direction, and
   the first irradiation unit, the second irradiation unit, and the third irradiation unit are arranged in a third direction intersecting both the first direction and the second direction.

* * * * *